(12) United States Patent
Grass et al.

(10) Patent No.: US 9,002,089 B2
(45) Date of Patent: Apr. 7, 2015

(54) IMAGE DATA REGISTRATION FOR DYNAMIC PERFUSION CT

(75) Inventors: Michael Grass, Buchholz in der Nordheide (DE); Alfonso Agatino Isola, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 185 days.

(21) Appl. No.: 13/643,167

(22) PCT Filed: Apr. 12, 2011

(86) PCT No.: PCT/IB2011/051579
§ 371 (c)(1),
(2), (4) Date: Oct. 24, 2012

(87) PCT Pub. No.: WO2011/138694
PCT Pub. Date: Nov. 10, 2011

(65) Prior Publication Data
US 2013/0039559 A1 Feb. 14, 2013

Related U.S. Application Data

(60) Provisional application No. 61/331,871, filed on May 6, 2010.

(51) Int. Cl.
*G06K 9/00* (2006.01)
*G06T 7/00* (2006.01)
*A61B 6/00* (2006.01)

(52) U.S. Cl.
CPC ..... *G06T 7/0026* (2013.01); *G06T 2207/10076* (2013.01); *G06T 2207/30104* (2013.01); *A61B 6/507* (2013.01)

(58) Field of Classification Search
None
See application file for complete search history.

(56) References Cited

U.S. PATENT DOCUMENTS

| 7,672,540 | B2 * | 3/2010 | Sun et al. | 382/294 |
|---|---|---|---|---|
| 8,090,180 | B2 * | 1/2012 | Maier et al. | 382/131 |
| 8,754,906 | B2 * | 6/2014 | Masumoto | 345/629 |
| 8,755,635 | B2 * | 6/2014 | Geiger et al. | 382/294 |
| 2008/0044104 | A1 * | 2/2008 | Gering | 382/294 |
| 2008/0137936 | A1 | 6/2008 | Boese et al. | |
| 2009/0080779 | A1 | 3/2009 | Chefd'hotel et al. | |
| 2009/0169080 | A1 | 7/2009 | Noordhoek | |
| 2009/0252378 | A1 | 10/2009 | Boese | |
| 2009/0263001 | A1 * | 10/2009 | Ding et al. | 382/131 |

OTHER PUBLICATIONS

Unser et al., The L2-polynomial spline pyramid, IEEE Trans. Pattern Anal. Mach. Intell., 1993, pp. 364-379, vol. 15.
M. Unser, Splines: A perfect fit for signal and image processing, IEEE Signal Process., 1999, pp. 22-38, Mag. 16.

(Continued)

*Primary Examiner* — Hadi Akhavannik

(57) ABSTRACT

A method of registering a 4D contrast enhanced image data set, wherein the 4D contrast enhanced image data set includes image data of the same volume of interest acquired at different timeframes with changing contrast enhancement, the volume of interest includes moving structure, and the different timeframes correspond to a predetermined motion phase of interest in different motion cycles of the moving structure, the method, comprising: registering image data corresponding to a plurality of the different timeframes with reference image from one of the timeframes.

19 Claims, 4 Drawing Sheets

(56) References Cited

OTHER PUBLICATIONS

Grass et al., 3D cone-beam CT reconstruction for circular trajectories, Phys. Med. Biol., 2000, pp. 329-347, vol. 45 No. 2.
Kybic et al., Fast parametric elastic image registration, IEEE Trans. Image Process. 2003, pp. 1427-1442, vol. 12.
Stantz et al., In Vivo Regional Myocardial Perfusion Measurements in a Porcine Model by ECG-Gated Multi-Slice Computed Tomography, In Proc. of SPIE Med. Imag. Conf., 2003, vol. 5031.
George RT et al., Multidetector Computed Tomography Myocardial Perfusion Imaging During Adenosine Stress, Journal of the American College of Cardiology, 2006, vol. 48, No. 1; 10 pages.
Klein et al., Evaluation of optimization methods for nonrigid medical image registration using mutual information and b-splines, IEEE Trans. Image Process., 2007, pp. 2879-2890, vol. 16.
Bruder et al., Spatio-temporal filtration of dynamic CT data using diffusion filter, in Proc. of SPIE Med. Imag. Conf., 2009, vol. 7258; 10 pages.
Chun et al., A simple regularizer for b-spline nonrigid image registration that encourages local invertibility, IEEE J. Sel. Top. Signal Process. 2009, pp. 159-169, vol. 3.
Klein et al., Adaptive stochastic gradient descent optimisation for image registration, International Journal of Computer Vision, 2009, pp. 227-239, vol. 81, No. 3.
Bhagalia et al., Accelerated nonrigid intensity-based image registration using importance sampling, IEEE Trans Med Imaging, Aug. 2009. pp. 1208-1216, vol. 28, No. 8. Abstract attached.
Breeuwer, M., et al.; Automatic quantitative analysis of cardiac MR perfusion images; 2001; Proc. of SPIE; vol. 4322; pp. 733-742.
Isola, A. A., et al.; Fully automatic nonrigid registration-based local motion estimation for motion-corrected iterative cardiac CT reconstruction; 2010; Med. Phys.; 37(3)1093-1109.
Isola, A. A., et al.; Image Registration and Perfusion Imaging: Application to Dynamic Circular Cardiac CT; 2010; IEEE Trans. on Nuclear Science Symposium; pp. 2362-2365.
"Image Feature Extraction" in: W. K. Pratt: "Digital Image Processing" 4th Ed.; Wiley-Interscience; 2007; pp. 535-541.

\* cited by examiner

IMAGE DATA REGISTRATION FOR DYNAMIC PERFUSION CT

CROSS REFERENCE TO RELATED APPLICATIONS

This application claims the benefit of U.S. provisional application Ser. No. 61/331,871 filed May 6, 2010, which is incorporated herein by reference.

The following generally relates to registering image data and is described with particular application to computed tomography (CT); however, other imaging applications are also contemplated herein.

A computed tomography (CT) scanner generally includes a stationary gantry and a rotating gantry. The rotating gantry is rotatably supported by the stationary gantry and carries an x-ray tube. A detector resides opposite the x-ray tube, across an examination region. The rotating gantry rotates around the examination region about a z-axis, and radiation emitted by the X-ray tube traverses the examination region and a patient anatomy therein, and is detected by the detector. The detector generates projection data indicative of the irradiated patient anatomy. A reconstructor reconstructs the projection data and generated reconstructed image data indicative of the irradiated patient anatomy.

CT, as well as other imaging modalities, can be used for perfusion imaging. Generally, perfusion imaging is an imaging approach for capturing information corresponding to the passage of fluid (e.g., blood, lymph, etc.) through anatomical tissue and quantifying the information to facilitate identifying a health state of the tissue or other tissue. For example, myocardial perfusion imaging can be used to measure oxygen supply of muscle tissue in the heart. As such, the heart of a patient can be imaged in three dimensions (3D) before and during injection of radio-opaque contrast material, and the differences in the reconstructed images can be attributed to the contrast material that is washed in the tissue. Muscle tissue can then be classified according to the degree of contrast material uptake, and pathologies can be detected, for example, myocardial infarction or coronary occlusion.

Prospectively ECG gated CT has been used for the myocardial perfusion imaging. With this technique, although a certain or particular cardiac phase (e.g., systole, diastole, etc.) is selected for the prospective gating, the motion states of the heart in the different time frames of the cardiac cycle may differ. This generally is due to the fact that the ECG gating relies on an electrical signal and not on the actual mechanical motion, and that the heart cycle length variation is not taking into account the prospective gating. As a consequence, the time frames of the dynamic measurements may not be aligned on a per voxel basis, and such misalignment may introduce artifacts into the temporal contrast agent uptake curves, which may lead to erroneous analysis results.

Aspects of the present application address the above-referenced matters and others.

According to one aspect, a method includes registering 4D contrast enhanced image data set. The method includes registering image data corresponding to a plurality of the different timeframes with reference image from one of the timeframes. The 4D contrast enhanced image data set includes image data of the same volume of interest acquired at different timeframes with changing contrast enhancement, the volume of interest includes moving structure, and the different timeframes correspond to a predetermined motion phase of interest in different motion cycles of the moving structure.

According to another aspect, a system includes a warping component that warps image data of a 4D image data set to register the image data with reference image data from the 4D image data set based on a gradient descent algorithm. The image data and the reference image data correspond to a same volume of interest and different time frames. The system further includes a similarity determiner that determines a value indicative of a similarity between the warped image data and the reference image data.

According to another aspect, a computer readable storage medium encoded with instructions which, when executed by a processor of a computer, cause the processor to: elastically register 4D ECG prospectively gated contrast enhanced image data based on a stochastic gradient descent optimization algorithm with an adaptive step size prediction in combination with a zero mean normalized cross-correlation similarity measure.

The invention may take form in various components and arrangements of components, and in various steps and arrangements of steps. The drawings are only for purposes of illustrating the preferred embodiments and are not to be construed as limiting the invention.

Figure 1:
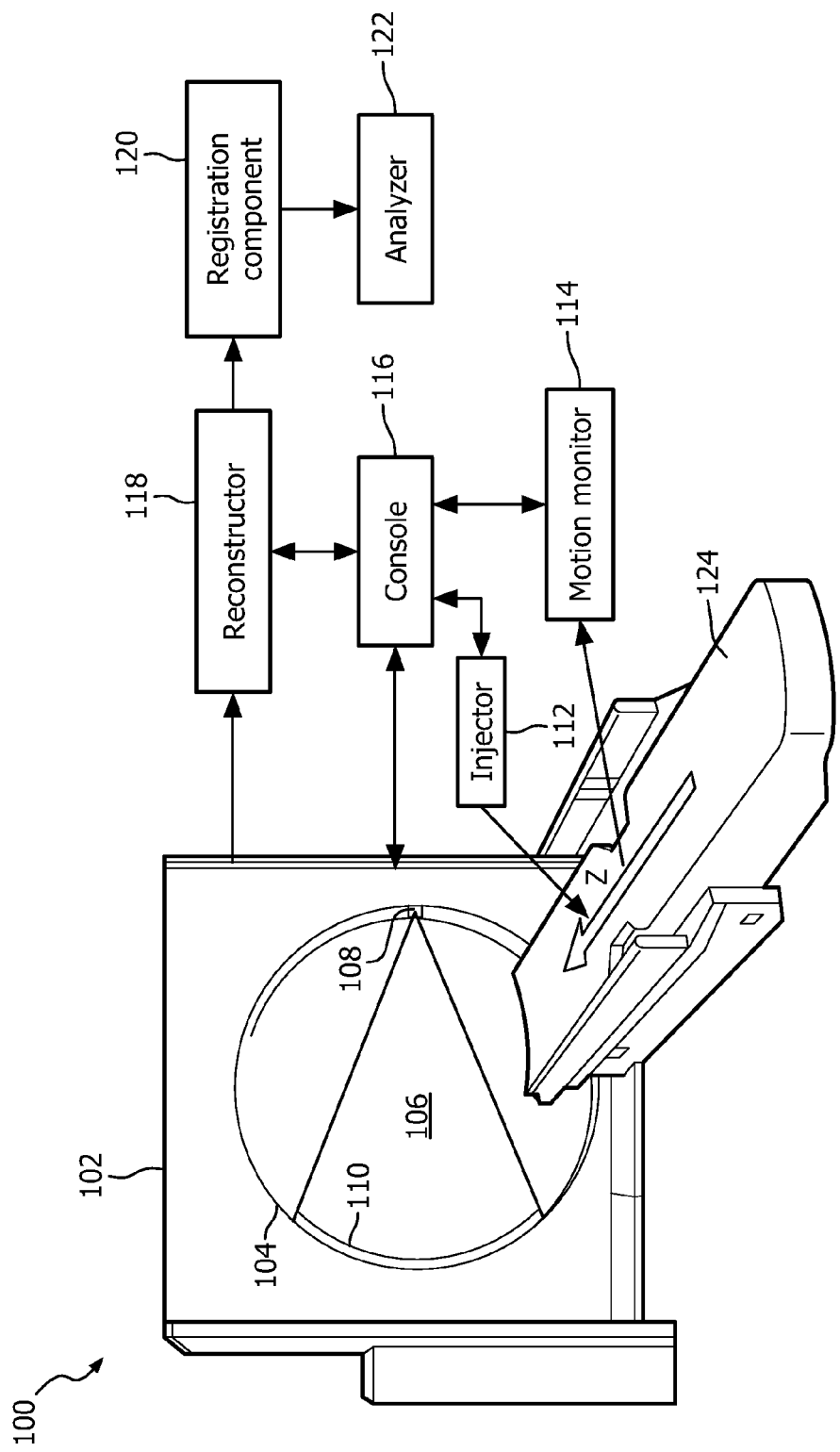
FIG. 1 illustrates an imaging system in connection with an image data registration component.

FIG. 1 illustrates an imaging system 100 such as a computed tomography (CT) scanner. The imaging system 100 includes a stationary gantry 102 and a rotating gantry 104, which is rotatably supported by the stationary gantry 102. The rotating gantry 104 rotates around an examination region 106 about a longitudinal or z-axis. In the illustrated embodiment, the rotating gantry 104 is configured to rotate fast enough for scanning a beating heart of a human, for example, for scanning the entire heart during a single cardiac cycle. In one instance, the illustrated rotating gantry 104 is configured to rotate at least at two hundred and seventy milliseconds (270 ms). The rotating gantry 104 can also rotate at lower and higher rotation times.

A radiation source 108, such as an x-ray tube, is supported by the rotating gantry 104 and rotates with the rotating gantry 104, and emits radiation. A source collimator collimates the radiation to form a cone, fan, wedge, or otherwise shaped radiation beam that traverses the examination region 106. A radiation sensitive detector array 110 located opposite the source 108 detects radiation that traverses the examination region 106 and generates projection data indicative thereof. In the illustrated embodiment, the radiation sensitive detector array 110 is sufficiently large enough to detect radiation traversing the entire heart of a patient at once. To do this, in one embodiment, the detector array 110 has at least two hundred and fifty-six (256) slices or rows of detectors. In other embodiment, the detector array 110 may have more or less slices or rows.

A motion monitor or sensor 114 is configured to sense a motion state of at least a predetermined volume of interest of a moving object or subject in the examination region 106 and generate a signal indicative thereof. The motion sensor 114 may include a cardiac and/or respiratory and/or other motion sensor. A general purpose computing system serves as an operator console 116, which includes human readable output devices such as a display and/or printer and input devices such as a keyboard and/or mouse. Software resident on the console 116 allows the operator to control the operation of the system 100, for example, by allowing the operator to select a scanning protocol (e.g., an ECG or otherwise gated contrast enhanced protocol that gates scanning based on the signal from the motion monitor 114), initiate scanning, etc. An injector 112 is configured to inject a contrast material(s), for example, for a contrast enhanced imaging procedure. The illustrated injector 112 is controlled by the console 116. In another instance, the contrast agent is manually administered.

A reconstructor 118 reconstructs projection data and generates volumetric image data indicative of the examination region 106. The reconstructor 118 can employ reconstruction algorithms that cover various angular ranges, for example, from one hundred eighty degrees (180°) plus a fan angel to three hundred and sixty degrees (360°) plus a fan angel and/or other ranges. A four dimensional (4D) data set can be reconstructed based on data acquired at different timeframes. In one instance, each timeframe may correspond to a different motion (e.g., cardiac, respiratory, etc.) cycle, or a sub-portion of the different motion cycles. The sub-portion may correspond to a predetermined and/or selected (e.g., cardiac, respiratory, etc.) phase(s) of interest within each cycle. With cardiac imaging, the phase may be systole, diastole, or other phase. In the case of contrast enhanced image data, the image data corresponding to the different motion cycle/timeframes may have different contrast enhancement representing the contrast uptake and wash out in tissue during scanning.

A support 124, such as a couch, supports the object or subject in the examination region 106. The support 124 can be used to variously position the object or subject in the examination region 106 with respect to x, y, and/or z axes before, during and/or after scanning. In one instance, the support 124 is used to position a volume of interest such as the heart or other tissue in the examine region 106, and then the entire volume of interest (or a substantial portion thereof) is scanned with the support 124 at the same position. An example of such a scan is a cardiac scan, such as a prospectively ECG gated contrast enhanced cardiac scan. For such a scan, the source collimator collimates the emitted radiation so as to produce a radiation beam with a suitable beam angle (x/y and/or z directions) to cover the volume of interest, the detector array has a suitable number of slices or detector rows along the z-axis to detect the radiation traversing the volume of interest, and the heart is scanned during a selected phase(s) each cardiac cycle or for certain selected sub-set of, such as less than each of, the cardiac cycles.

A registration component 120 registers the 4D image data or a predetermined sub-portion thereof. As noted above, the 4D image data may include image data corresponding to different motion cycles and thus timeframes. With contrast enhanced studies, the image data corresponding to the same motion phase within different motion cycles and timeframes may have different contrast enhancement, reflecting contrast uptake and wash out over the course of the imaging procedure and time. As described in greater detail below, in one instance, the registration algorithm includes an iterative elastic registration based on a gradient with a similarity metric that facilitates determining when image data is suitably registered. With contrast enhanced data, such an algorithm may take into account variations of contrast agent concentration across different time frames and/or inconsistent motion states. Such an algorithm may mitigate artifacts due to geometric misalignment, thereby providing higher quantitative accuracy for various imaging procedures such as myocardial perfusion CT imaging.

An analyzer 122 can be used to analyze the registered image data. With perfusion scans, the analyzer 122 can be used to generate perfusion maps and/or perfusion parameters such as time to peak, area under the curve (i.e., blood volume passing through the tissue), local peak intensity or enhancement, average rising slope, maximum up-slope, time to maximum up-slope, etc. Such information may be generated on a per voxel basis, a per region of interest basis, or other basis, for example, along the temporal axis. The generated perfusion maps and/or perfusion parameters can be variously presented, for example, as color coded perfusion maps, graphs, etc., stored in memory, filmed, conveyed for processing, etc.

It is to be appreciated that the registration component 120 and/or the analyzer 122 may be part of the system 100 (as shown) or remote therefrom, for example, in a computing system such as a workstation or the like. In either instance, one or more processors may execute computer readable instructions encoded and/or embodied on local or remote computer readable storage medium such as memory to implement the registration component 120 and/or the analyzer 122.

Figure 2:
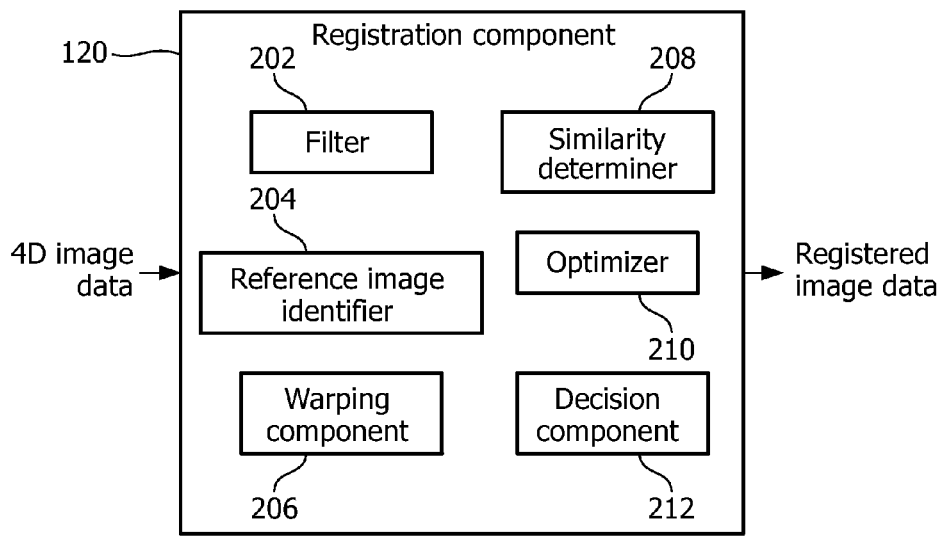
FIG. 2 illustrates an example registration component.

FIG. 2 illustrates an example of the registration component 120.

Figure 3:
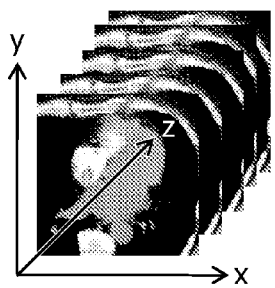
FIG. 3 illustrates example spatial filtering of 4D image data.
Figure 4:
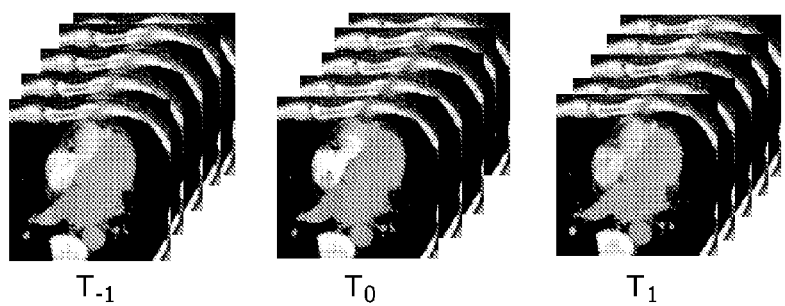
FIG. 4 illustrates example temporal filtering of 4D image data.

The illustrated registration component 120 includes a filter 202, which is employed to filter 4D image data that includes image data acquired at different moments in time, or image data corresponding to different timeframes. The illustrated filter 202 is configured to spatially filter the image data and then temporally filter the image data. FIG. 3 shows an example of spatially filtering 4D image data corresponding to a prospectively ECG gated contrast enhanced cardiac perfusion scan along spatial coordinates (x, y, and z), and FIG. 4 shows an example of temporally filtering the 4D image data temporal coordinates (time). Returning to FIG. 2, such multi-dimensional image filtration may increase the signal-to-noise ratio (SNR) of the image data while maintaining spatial and temporal sharpness of the image data. Increasing the SNR (i.e., decreasing image noise) may lead to a more accurate quantitative analysis of myocardial perfusion. In another embodiment, the filter 202 is omitted or another filter is utilized. As example of a suitable filter is discussed in H. Bruder et al., "Spatio-temporal filtration of dynamic CT data using diffusion filter", in Proc. of SPIE Med. Imag. Conf., vol. 7258. 2009.

A reference image identifier 204 identifies reference image data in the 4D data set. With respect to 4D contrast enhanced image data, the reference image identifier 204 may do this by identifying the timeframe or image data having a highest contrast (peak) enhancement. This can be done automatically, for example, from peak enhancement curves or otherwise. Generally, the image data corresponding to the different scanned cardiac cycles will have different amounts of contrast enhancement as the contrast is taken up and washed out, and the image data with the highest contrast uptake corresponds to the time when both heart chambers are completely filled of contrast agent and will likely show greater border detail relative to the other image data. This timeframe can be automatically identified by the registration component 120, for example, by finding the timeframe with the maximum image energy. In another instance, the reference image identifier 204 identifies the reference image data based on a signal indicative of user selected image data and/or otherwise.

A warping component 206 warps or transforms the 4D image data based on the reference image data. In the illustrated embodiment, the warping component 206 employs an elastic or non-rigid algorithm. In other embodiment, a rigid algorithm is additionally or alternatively employed. The warping component 206 may warp the image data once or multiple times, for example, by warping previously warped image data. For example, when it is determined that the warped image data and the reference are not structurally similar enough, the warping component 206 may warp the warped image data. A similarity determiner 208 determines a value indicative of a similarity between warped imaged data and the reference image data. An optimizer 210 facilitates minimizing similarity criterion.

A decision component 212 determines when a suitable registration has been reached. If one has not been reached, the registration component 120 warps the warped image data, the similarity determiner 208 determines another value, and the decision component 120 determines if a suitable registration has been reached based on the new value. These steps may be repeated until the registration is determined to be acceptable. In one instance, the decision component 212 determines a difference value between the value and a value determined for a previous warping of the image data compares the difference value with a predetermined threshold. In another instance, the decision component 212 compares the value with a predetermined (relative or absolute) threshold value. In yet another instance, the decision component 212 determines when a predetermined number of iterations have been performed on the image data. Other criteria my additionally or alternatively be used to determine when a suitable registration is reached.

Figure 5:
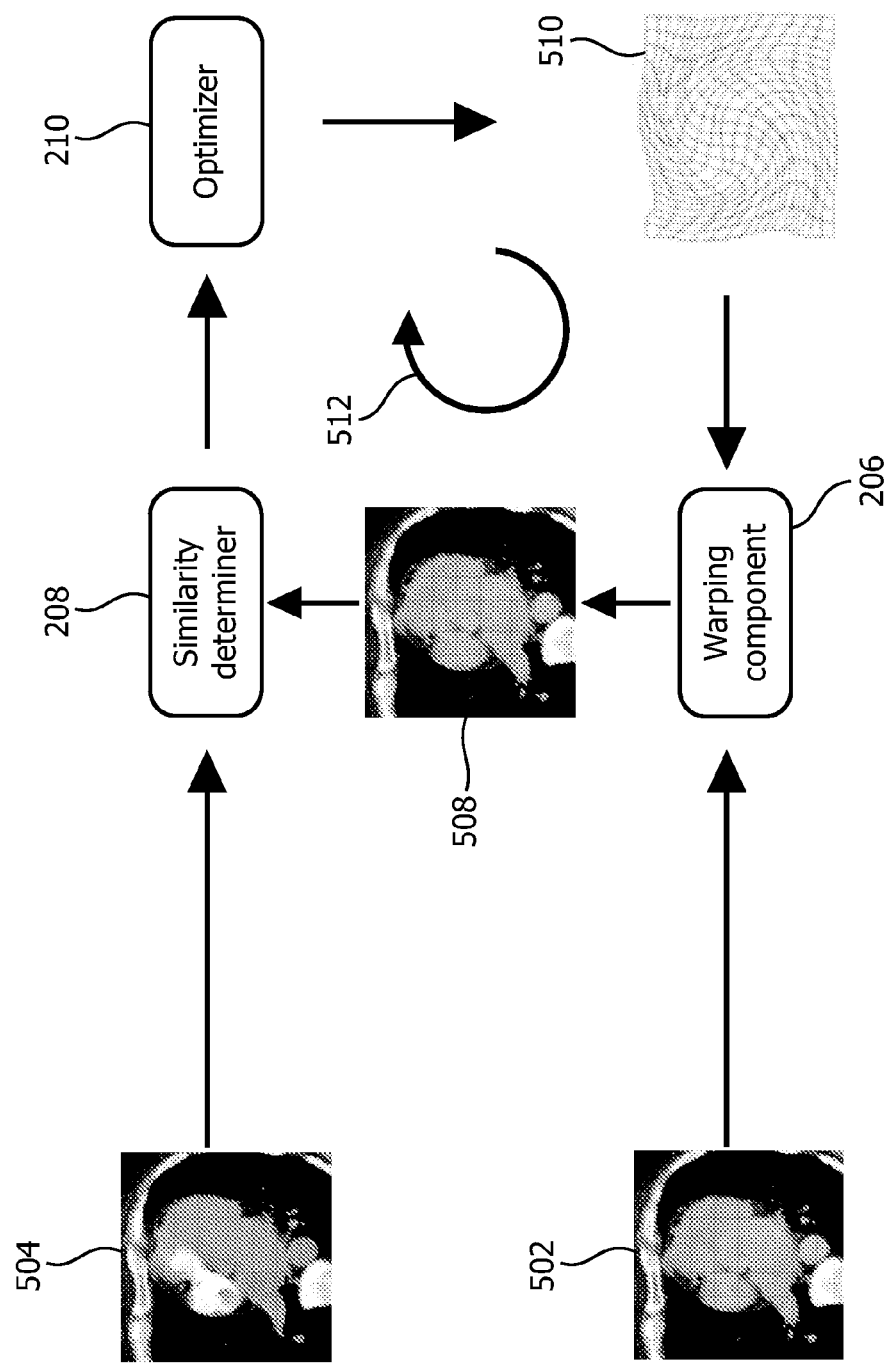
FIGS. 5 and 6 illustrate an example registration.
Figure 6:
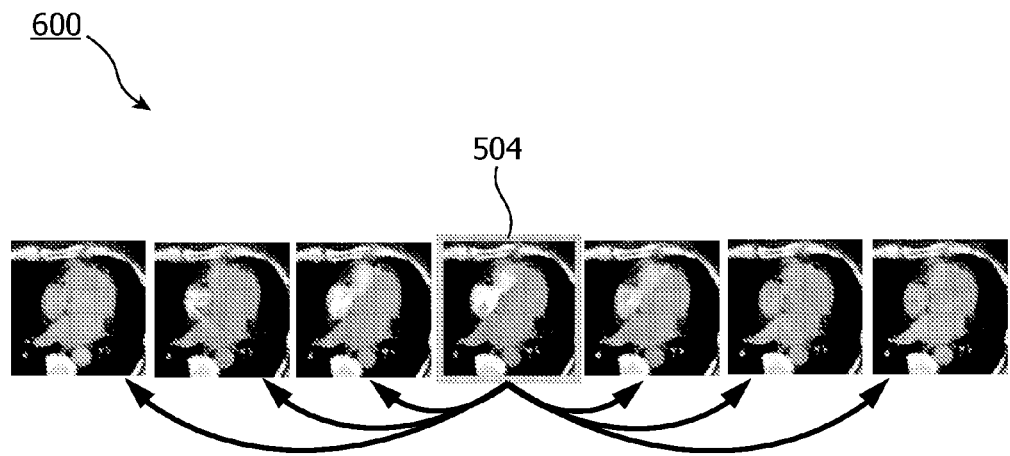

FIGS. 5 and 6 illustrate an example registration by the registration component 120. In this example, the registration component 120 determines a deformation field that satisfies Equation 1:

$$fw(x)=ft(g(x))=fr,$$

wherein fw represents the warped image data, ft represents the image data being registered with the reference image data, g represents the deformation field, and fr represents the reference image data. The registration component 120 may utilize all or a sub-set of voxel-intensity values of the images being registered.

In FIG. 5, image data 502 is being registered with reference image data 504. In this example, the warping component 206 includes an interpolator that warps the image data 502, generating warped or deformed image data 508. A suitable interpolation algorithm includes a cubic B-spline or other algorithm. The similarity component 208 determines a similarity value between the warped image data 508 and the reference image data 504. In the illustrated embodiment, the similarity criterion includes a zero mean normalized cross correlation between the images fr and ft. The optimizer 210 attempts to find the best deformation g that minimizes a similarity criterion. A suitable optimizer includes an adaptive stochastic gradient descent optimization. This criterion is well-suited to handle the varying contrast agent concentration in the 4D image data. A correspondence between the discrete and continuous versions of the images and of the deformation field g 510 can be established using cubic B-Splines. As noted herein, the registration may include one or more iterations 512. As shown in FIG. 6, the image data from one or more of the timeframes 600 is registered based on and/or with the reference image data 504.

In the illustrated embodiment, the adaptive stochastic gradient descent optimization algorithm is applied with adaptive step size prediction. A suitable optimization algorithm with step size prediction is discussed in S. Klein, J. P. W. Pluim, M. Staring and M. A. Viergever, "Adaptive stochastic gradient descent optimisation for image registration", International Journal of Computer Vision, 81(3), pp. 227-239, 2009. Such an algorithm may decrease computation time per iteration, without affecting the rate of convergence, final precision, or robustness. This algorithm is similar to a deterministic gradient descent with the distinction that the gradient of the similarity criterion is replaced by an approximation. A stochastic approximation of the derivative of the similarity criterion can be determined by using a new, randomly selected subset of voxels in every iteration of the optimization process. In this way, a bias in the approximation error is avoided.

The speed and accuracy of the registration may depend on the quality of the gradient approximation obtained via random sampling. The subset of random voxel locations can be determined using either uniform sampling or non-uniform sampling, which may improve the gradient approximations. The image edges may strongly influence intensity-based registration estimates. As such, a sampling distribution that emphasizes image edges can be used to improve the gradient approximations. In one instance, a binary mask is used to randomly sample only voxels which have the highest image gradient magnitudes. Another suitable approach for random sampling is described in Bhagalia R, Fessler J A, Kim B, "Accelerated nonrigid intensity-based image registration using importance sampling," IEEE Trans Med Imaging, 2009 August; 28(8):1208-16.

A multi-resolution approach can be applied to improve the robustness and the efficiency of the registration algorithm. With such an algorithm, the registration can first be performed using coarse subsampled images and determine a deformation field with reduced number of degrees of freedom. Subsequently, the results can be propagated to the next finer level. This iterative procedure may expand, alternately, the grids of the B-spline control points of the images and of the deformation field until the finest level is reached. A suitable multi-resolution approach is discussed in M. Unser, A. Aldroubi, and M. Eden, "The L2-polynomial spline pyramid," IEEE Trans. Pattern Anal. Mach. Intell. 15, 364-379 1993. This approach uses 3D B-spline reduce/expand operators of factor of two (2) to build a pyramid, or a set of gradually reduced versions of the original images and the deformation field, which is optimal.

In instances in which there is a high degree of freedom in the registration, there may inherently be an ill-posed problem that could lead to unrealistic folding of the deformation fields in the absence of suitable constraints. As such, various constraints may be employed when estimating the deformation field g. For example, in one instance one constraint may be that the deformation field g is invertible as human organ and tissue motion is invertible. One suitable approach well-suited for 3D registrations can be found in S. Y. Chun and J. A. Fessler, "A simple regularizer for b-spline nonrigid image registration that encourages local invertibility," IEEE J. Sel. Top. Signal Process. 3, 159-169 2009. The penalty function disclosed in Fessler encourages positive Jacobian determinants by bounding the differences of two adjacent deformation coefficients in the x, y, z direction. By constraining the differences only instead of the coefficients, even large deformations g with gradients within the bounds are included in the search solution space.

Figure 7:
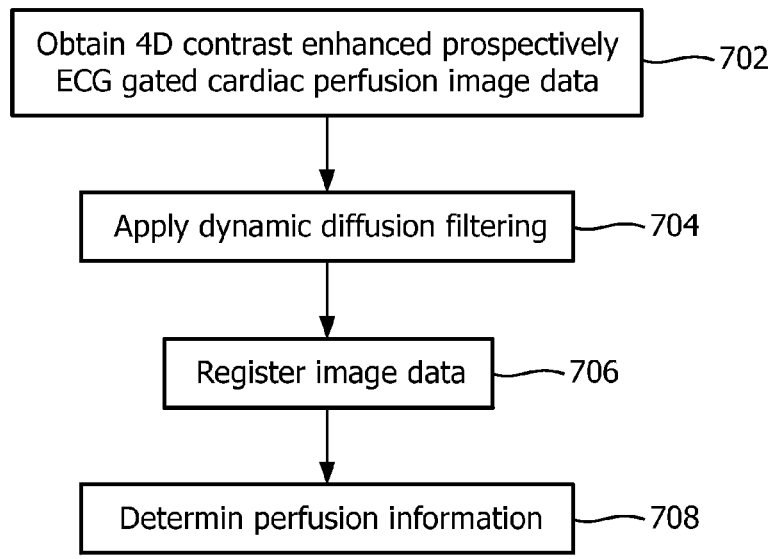
FIG. 7 illustrates an example method.

FIG. 7 illustrates a method. For this example, the registration component 120 registers 4D image data acquired via a contrast enhanced prospective ECG gated cardiac perfusion scan. Such a scan is gated based a predetermined cardiac phase(s) such as the systolic phase, the diastolic phase, and/or other cardiac phase in each cardiac cycle or heart beat (i.e., within each R-R interval). The phase(s) may be selected by the operator of the scanner, identified via the selected imaging protocol, and/or otherwise determined. Furthermore, the scan may be gated such that the phase(s) of the heart is scanned every heart cycle, every other heart cycle, or some other number of heart cycles less than every heart cycle. Scanning can be initiated prior to, at, or shortly after administration of the contrast agent.

At 702, 4D perfusion image data is obtained. At 704, dynamic diffusion filtering is applied to the 4D data set as described in connection with FIG. 2 or otherwise. At 706, the filtered image is registered as described herein. For example, in one instance this includes elastically registering image data using reference image data using a stochastic gradient descent optimization method with adaptive step size prediction in combination with a zero mean normalized cross-correlation similarity measure. At 708, the resulting registered image data is processed. This includes determining various perfusion maps and/or parameters. Using this method, artifacts due to geometric misalignment may be removed or reduced when registering contrast enhance image data of a moving object or anatomical structure. As such, perfusion applications such as myocardial perfusion CT imaging may provide data well-suited for relatively higher quantitative accuracy.

The above described acts may be implemented by way of computer readable instructions, which, when executed by a computer processor(s), causes the processor(s) to carry out the acts described herein. In such a case, the instructions are stored in a computer readable storage medium such as memory associated with and/or otherwise accessible to the relevant computer.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method of registering a 4D contrast enhanced image data set of a perfusion scan with enhancement by a contrast agent, wherein the 4D contrast enhanced image data set includes image data of the same volume of interest acquired at different timeframes with changing contrast enhancement, the volume of interest includes moving structure, and the different timeframes correspond to a predetermined motion phase of interest in different motion cycles of the moving structure, the method, comprising:
    registering image data corresponding to a plurality of the different timeframes with reference image from one of the timeframes, wherein the image data is registered using an iterative gradient based registration algorithm and a similarity measure, wherein the registration algorithm is based on stochastic gradient descent optimization algorithm, and wherein the similarity measure includes a zero mean normalized cross-correlation similarity measure.

2. The method of claim 1, wherein the zero mean normalized cross-correlation similarity measure handles varying contrast agent concentration in the 4D contrast enhanced image data set.

3. The method of claim 1, registering image data, comprising:
    warping image data for a particular timeframe to fit the reference image data;
    determining a value indicative of a similarity between the warped image data and the reference image data; and
    registering the image data to the reference image data when the value satisfies a predetermined criteria and warping the warped image data when the value does not satisfy the predetermined criteria.

4. The method of claim 3, wherein the predetermined criteria includes a threshold value.

5. The method of claim 3, wherein the predetermined criteria includes a maximum number of iterations.

6. The method of claim 1, further comprising:
    filtering the 4D image data prior to registering the 4D image data, wherein the filtering includes spatially filtering the 4D image data set and temporally filter the 4D image data.

7. The method of claim 1, further comprising:
    generating at least one of a parameter map or a perfusion parameter based on the registered 4D image data set.

8. The method of claim 1, wherein the 4D image data set corresponds to a prospectively ECG gated contrast enhanced perfusion scan.

9. The method of claim 1, wherein the reference image data corresponds to image data having a predetermined contrast enhancement of interest.

10. The method of claim 1, wherein the 4D image data set includes cardiac image data and corresponds to a particular predetermined cardiac phase of interest.

11. A system, comprising:
    a warping component that warps image data of a 4D image data set to register the image data with reference image data from the 4D image data set based on a stochastic gradient descent optimization algorithm with an adaptive step size prediction in combination with a zero mean normalized cross-correlation similarity measure, wherein the image data and the reference image data correspond to a same volume of interest and different time frames
    a similarity determiner that determines a value indicative of a similarity between the warped image data and the reference image data.

12. The system of claim 11, wherein the image data is iteratively warped until the value satisfies predetermined similarity criteria.

13. The system of claim 11, further comprising:
    a filter configured to spatially filter the image data.

14. The system of claim 13, wherein the filter is configured to temporally filter the image data.

15. The system of claim 11, further comprising:
    a reference image identifier that identifies the reference image data in the 4D data set based on a timeframe having a peak contrast enhancement in the 4D image data set.

16. The system of claim 15, wherein the peak contrast enhancement is determined based on an energy of the image data.

17. The system of claim 11, further comprising:
    an analyzer that generate at least one of a perfusion map or a perfusion parameter based on the registered image data.

18. A non-transitory computer readable storage medium encoded with computer executable instructions, which, when executed by a processor of a computer, cause the processor to perform the steps of claim 1.

19. A method of registering a 4D image data set of a perfusion scan, wherein the 4D image data set includes image data of the same volume of interest acquired at different timeframes with changing contrast enhancement by a contrast agent, the volume of interest includes a moving structure, and the different timeframes correspond to a predetermined motion phase of interest in different motion cycles of the moving structure, the method, comprising:
    warping image data of a selected timeframe to fit reference image data;

determining a measure of similarity between the warped image data and the reference image data and the measure of similarity includes a zero mean normalized cross-correlation; and registering the image data to the reference image data using an iterative gradient based registration algorithm and the similarity measure when the measure of similarity satisfies a predetermined criteria and warping the warped image data when the measure of similarity does not satisfy the predetermined criteria.

* * * * *